US00PP23240P2

(12) United States Plant Patent
Danziger

(10) Patent No.: US PP23,240 P2
(45) Date of Patent: Dec. 4, 2012

(54) ***PETUNIA* PLANT NAMED 'DRAY263'**

(50) Latin Name: *Petunia sensu Wijsman*
Varietal Denomination: DRAY263

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 27 days.

(21) Appl. No.: 13/068,523

(22) Filed: May 13, 2011

(51) Int. Cl.
*A01H 5/00* (2006.01)

(52) U.S. Cl. ..... Plt./356.21; Plt./356.1

(58) Field of Classification Search ..... Plt./356.21, Plt./356.1
See application file for complete search history.

*Primary Examiner* — Susan McCormick Ewoldt
(74) *Attorney, Agent, or Firm* — Cassandra Bright

(57) ABSTRACT

A new and distinct *Petunia* cultivar named 'DRAY263' is disclosed, characterized by a trailing/mounding plant habit. The new variety has a distinctive round flower shape, and red/purple flower color. The new variety is a *Petunia*, normally produced as an outdoor garden or container plant.

2 Drawing Sheets

Figure 1:
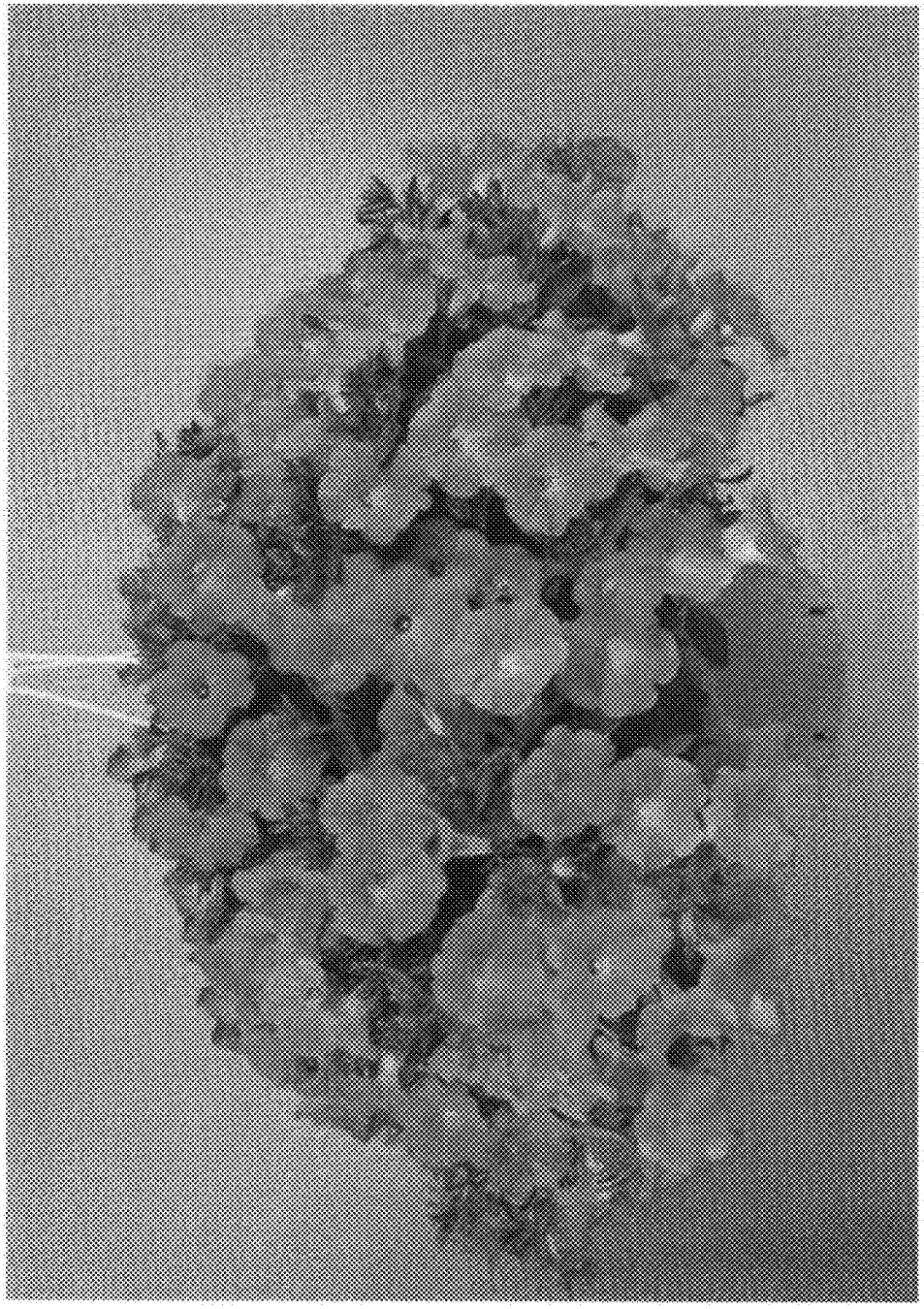

Latin name of the genus and species: *Petunia sensu Wijsman.*

Variety denomination: 'DRAY263'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during November 2007.

The seed parent is the unpatented, proprietary seedling variety referred to as *Petunia sensu Wijsman* 'Pe-2852' The pollen parent is the unpatented proprietary seedling variety referred to as *Petunia sensu Wijsman* 'Pe-123'. The new variety was discovered in March 2008 by the inventor in a group of seedlings resulting from the 2007 crossing, in a research greenhouse in Moshav Mishmar Hashiva, Israel.

Asexual reproduction of the new cultivar 'DRAY263' by vegetative cuttings was first performed at a research greenhouse in Moshav Mishmar Hashiva, Israel in March 2008 and has shown that the unique features of this cultivar are stable and reproduced true to type in successive generations.

SUMMARY OF THE INVENTION

The cultivar 'DRAY263' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DRAY263' These characteristics in combination distinguish 'DRAY263' as a new and distinct *Petunia* cultivar:

1. Mounded and trailing plant habit
2. Very round flower shape.
3. Distinctive red-purple flower.

Plants of the new cultivar 'DRAY263' are similar to plants of the seed parent, *Petunia sensu Wijsman* 'Pe-2852' in most horticultural characteristics, however, plants of the new cultivar 'DRAY263' have a more mounded plant habit, and different color flowers.

Plants of the new cultivar 'DRAY263' are similar to plants of the pollen parent, *Petunia sensu Wijsman* 'Pe-123' in most horticultural characteristics, however, plants of the new cultivar 'DRAY263' produce somewhat less lateral branches, and smaller flowers. Additionally, the new variety produces red-purple flowers whereas the pollen parent produces white flowers.

COMMERCIAL COMPARISON

Plants of the new cultivar 'DRAY263' are comparable to the variety *Petunia* 'DANCASDEEP' U.S. Plant Pat. No. 17,020. The two *Petunia* varieties are similar in most horticultural characteristics however, the new variety 'DRAY263' differs in having pink flowers, compared to red flowers on this comparator variety. Additionally 'DRAY263' produces smaller flowers and more lateral branches than 'DANCASDEEP'. Plants of 'DRAY263' have a mounded/trailing plant habit, whereas plants of 'DANCASDEEP' have a trailing plant habit.

Plants of the new cultivar 'DRAY263' are comparable to the unpatented variety *Petunia* 'Cascadias White'. The two *Petunia* varieties are similar in most horticultural characteristics however, the new variety 'DRAY263' differs in having pink flowers, compared to white flowers on this comparator variety. Additionally 'DARAY263' produces smaller flowers and slightly less lateral branches than 'DANCASDEEP'.

BRIEF DESCRIPTION OF THE PHOTOGRAPHS

The accompanying photograph in FIG. 1 illustrates in full color a typical plant of 'DRAY263' grown in a greenhouse, in a 13 cm pot. Age of the plant photographed is approximately 7 weeks from a rooted cutting.

Figure 2:
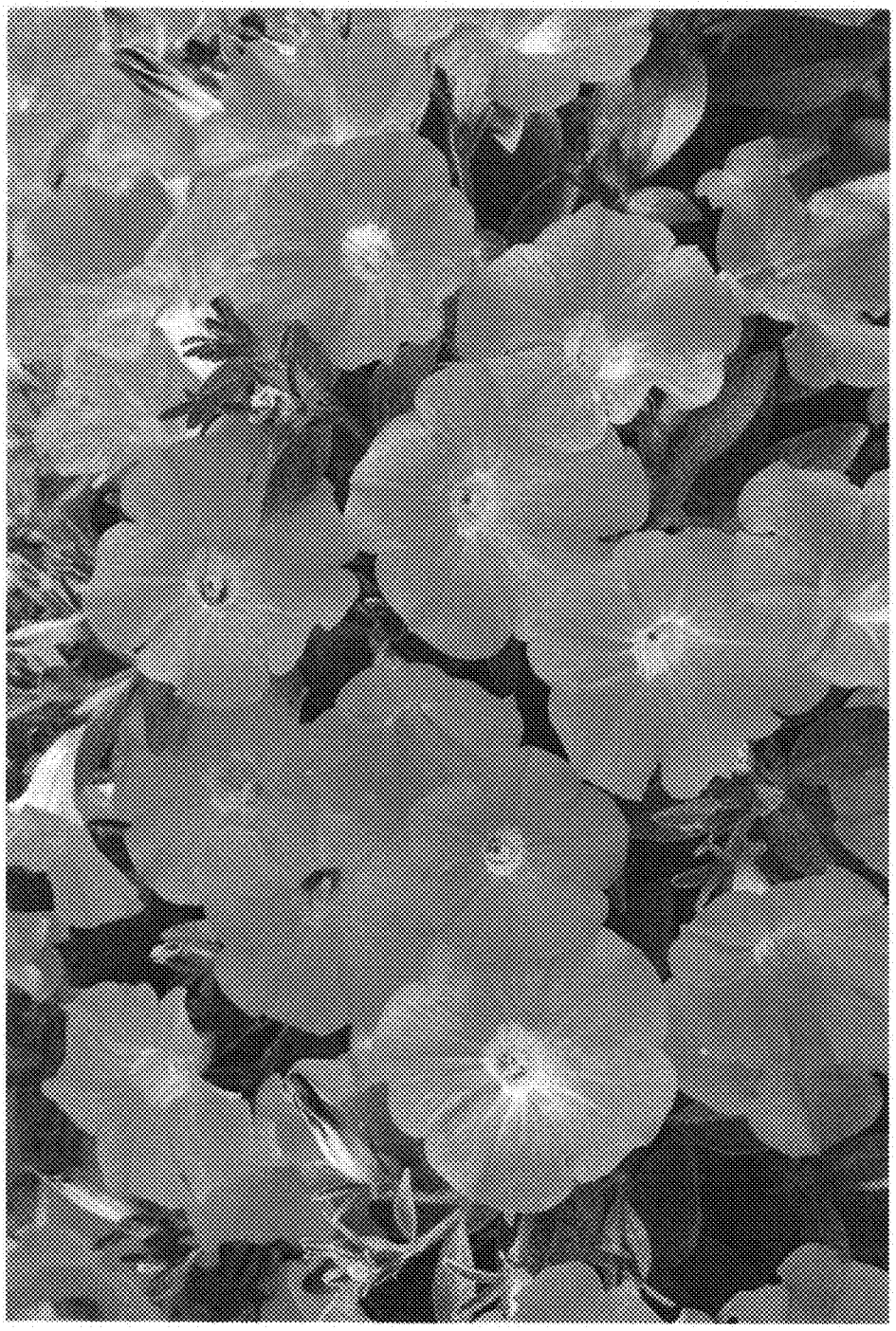

FIG. 2 illustrates in full color a close up of a typical bloom of 'DRAY263'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DRAY263' plants grown outdoors during Autumn in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu Wijsman* 'DRAY263'.

PROPAGATION

Time to initiate roots: 10 to 14 days at approximately 18-35° C.

Root description: Fibrous.

PLANT

Age of plant described: Approximately 30 days.
Growth habit: Mounded-Trailing.
Pot size of plant described: 12 cm.
Height: To top of flowers: Approximately 15 cm.
Plant spread: 30-40 cm.
Growth rate: Moderate.
Branching characteristics: Moderately free branches.
Length of primary lateral branches: Average 20 cm.
Diameter of lateral branches: 0.7 cm.
Quantity of primary lateral branches: 15-25.
Characteristics of primary lateral branches:
- *Diameter.*—0.7 cm.
- *Color.*—Near RHS Green 139-A.
- *Texture.*—Pubescent.
- *Strength.*—Flexible.

Internode length: 3-5 cm.

FOLIAGE

Leaf:
- *Arrangement.*—Opposite.
- *Quantity.*—Approximately 10 per branch.
- *Average length.*—5 cm.
- *Average width.*—3 cm.
- *Shape of blade.*—Oval.
- *Apex.*—Rounded.
- *Base.*—Acute.
- *Margin.*—Entire.
- *Pubescence.*—Pubescent, both surfaces.
- *Angle of attachment.*—90°.
- *Aspect.*—Flat.
- *Color.*—Young foliage upper side: RHS 139-A. Young foliage under side: RHS 139-A. Mature foliage upper side: RHS 139-A. Mature foliage under side: RHS 139-A.
- *Venation.*—Type: Pinnate. Venation color upper side: RHS 139-A. Venation color under side: RHS 139-A.
- *Petiole.*—Not present.

FLOWER

Natural flowering season: All year in Mediterranean climates.
Days to flowering from rooted cutting: 10-20 days.
Inflorescence and flower type and habit: Terminal, Single, Salverform, Erect.
Rate of flower opening: 2 to 3 days from bud to fully opened flower.
Flower longevity on plant: 3-6 days.
Approximate quantity of flowers per plant: 20.
Persistent or self-cleaning: Self-cleaning.
Bud:
- *Shape.*—Tubular.
- *Length.*—2-3 cm.
- *Diameter.*—0.5-1 cm.
- *Color RHS.*—Near RHS Red-Purple N66D with Green-Yellow 1B.

Flower size:
- *Diameter.*—5 cm.
- *Flower tube length.*—2.5 cm.
- *Flower tube diameter at distal end.*—1.3 cm.
- *Flower tube diameter at proximal end.*—0.7 cm.

Corolla/petals:
- *Length from throat.*—2.5 cm.
- *Width.*—2.5 cm.
- *Quantity.*—5.
- *Texture.*—Smooth.
- *Apex.*—Blunt.
- *Margin.*—Entire.

Color: When opening: Upper surface: Near RHS Red-Purple N57B. Lower surface: Near RHS Red-Purple N57C. Fully opened: Upper surface: Near RHS Red-Purple N57C. Lower surface: Near RHS Red-Purple N66D. Flower throat (inside): Near RHS Green-Yellow 1B. Flower throat, veins: Near RHS Green-Yellow 1A. Flower tube (outside): Near RHS Green-Yellow 1B. Flower tube, veins: Near RHS Green-Yellow 1A. Fading: Petals fading to: Near RHS Red-Purple N57D.
- *Calyx/sepals.*—
- *Quantity per flower.*—5.
- *Shape.*—Elliptic.
- *Length.*—2.5 cm.
- *Width.*—0.7 cm.
- *Apex.*—Truncate.
- *Base.*—Cuneate.
- *Margin.*—Entire.
- *Texture.*—Lustrous.
- *Color.*—Upper Surface: Near RHS Green 139-A. Lower Surface: Near RHS Green 139-A.

Peduncle:
- *Length.*—2.5-3 cm.
- *Diameter.*—0.4 cm.
- *Color.*—Near RHS Green 139A.
- *Orientation.*—45 degree and, straight.

Fragrance: No.

REPRODUCTIVE ORGANS

Stamens:
- *Number.*—5.
- *Filament length.*—1.5 cm.

Anthers: Length: 0.1 cm. Shape: Round. Color: Near RHS White 155D. Pollen: Color: Near RHS White 155D. Quantity: Abundant.

Pistil:
- *Number.*—1.
- *Length.*—1.5 cm.
- *Style.*—Length: 1.4 cm. Color: Near RHS Green139-C.

*Stigma*.—Shape: Round. Color: Near RHS Green139-C. Ovary Color: Near RHS Green139-C.

OTHER CHARACTERISTICS

Seeds and fruits: Numerous minute dark seeds.

Disease/pest resistance: Neither resistance nor susceptibility to pathogens and pests common to *Petunia* have been observed.

Temperature tolerance: The new variety tolerates temperatures between 5 to 40° C.

What is claimed is:

1. A new and distinct cultivar of *Petunia* plant named 'DRAY263' as herein illustrated and described.

* * * * *